US00PP21479P3

(12) United States Plant Patent
Fleming

(10) Patent No.: US PP21,479 P3
(45) Date of Patent: Nov. 16, 2010

(54) ***HIBISCUS* PLANT NAMED 'STARDUST'**
(50) Latin Name: *Hibiscus moscheutos*
Varietal Denomination: Stardust

(76) Inventor: David Whitman Fleming, Lincoln, NE (US); Gretchen Angela Zwetzig, legal representative, 267 N. Strathmore Ave., Lindsay, CA (US) 93247

( * ) Notice: Subject to any disclaimer, the term of this patent is extended or adjusted under 35 U.S.C. 154(b) by 0 days.

(21) Appl. No.: 12/317,181

(22) Filed: Dec. 18, 2008

(65) Prior Publication Data

US 2010/0162448 P1 Jun. 24, 2010

(51) Int. Cl.
*A01H 5/00* (2006.01)

(52) U.S. Cl. ..... Plt./257
(58) Field of Classification Search ..... Plt./257
See application file for complete search history.

*Primary Examiner*—Susan B McCormick Ewoldt

(57) ABSTRACT

A new and distinct cultivar of winter hardy *hibiscus* plant named "Stardust" is the result of a unique hybridization. This new and distinct cultivar is characterized primarily to its novelty by, its extreme cold hardiness to Zone 4, large, thick-textured, heavily streaked and speckled, red and pink flowers and its "maple-shaped" foliage with a bronze coloration, compactness of approximately 2½ feet, its vigorous and uniform breaking habit, and its floriferous nature from midsummer until frost.

2 Drawing Sheets

Latin name: *Hibiscus moscheutos.*
Varietal denomination: 'Stardust' hardy *Hibiscus.*

BACKGROUND OF THE NEW PLANT

The new plant of this invention is the result of a unique hybridization, with the breeding achievement being evidenced in the outstanding combination of characteristics exhibited by this new and distinct *Hibiscus* plant, which include:

(a) Refined, 3-5 lobed "maple-shaped" leaves of a bronze color and relatively smooth margins which combined compliments the landscape;
(b) Medium to large-sized flowers that are outstanding for their red and pink colored, heavily streaked and speckled petals;
(c) The plant being very floriferous with flowers that stay open for at least one to two days;
(d) The plant being small to medium-sized but vigorous with compact and uniform breaking action which gives it unique landscape utility; and
(e) The plant being so hardy that it can consistently withstand winter temperatures of at least −30 degrees Fahrenheit.

SUMMARY OF THE INVENTION

'Stardust' was the result of a 40-year breeding program. Its ancestry includes *Hibiscus moscheutos* and *Hibiscus coccineus*. More specifically, the plant resulted from multiple crossings with an unnamed, Fleming-bred *Hibiscus moscheutos* (non patented) and an unnamed Fleming-bred *Hibiscus coccineus* (non patented). The seedling which most nearly met all of the above standards was selected.

This new plant first bloomed in the summer of 1998 and was selected by David Fleming and Gretchen Zwetzig on David Fleming's property located at 8101 S. 14th St. 68512 Lincoln, Nebr. (previous address for applicants). Asexual propagation of the plant by cuttings and root division in Lincoln, Nebr. has shown that the unique and distinguishing features of the plant are faithfully transmitted from generation to generation and appear to be fixed.

Since its origin, the plant has bloomed from midsummer until frost, while exhibiting the aforementioned distinctive characteristics. This hardy *Hibiscus* plant greatly contributes to the market with its, sheer beauty and utter refinement, its compact growth habit, its enhanced resistance to disease and insects, its stability through extremes in rain and drought, and its extreme hardiness.

BRIEF DESCRIPTION OF THE DRAWINGS

The flower and foliage of the cultivar at 2½ years of age are shown in the attached drawings. More specifically.

Figure 1:
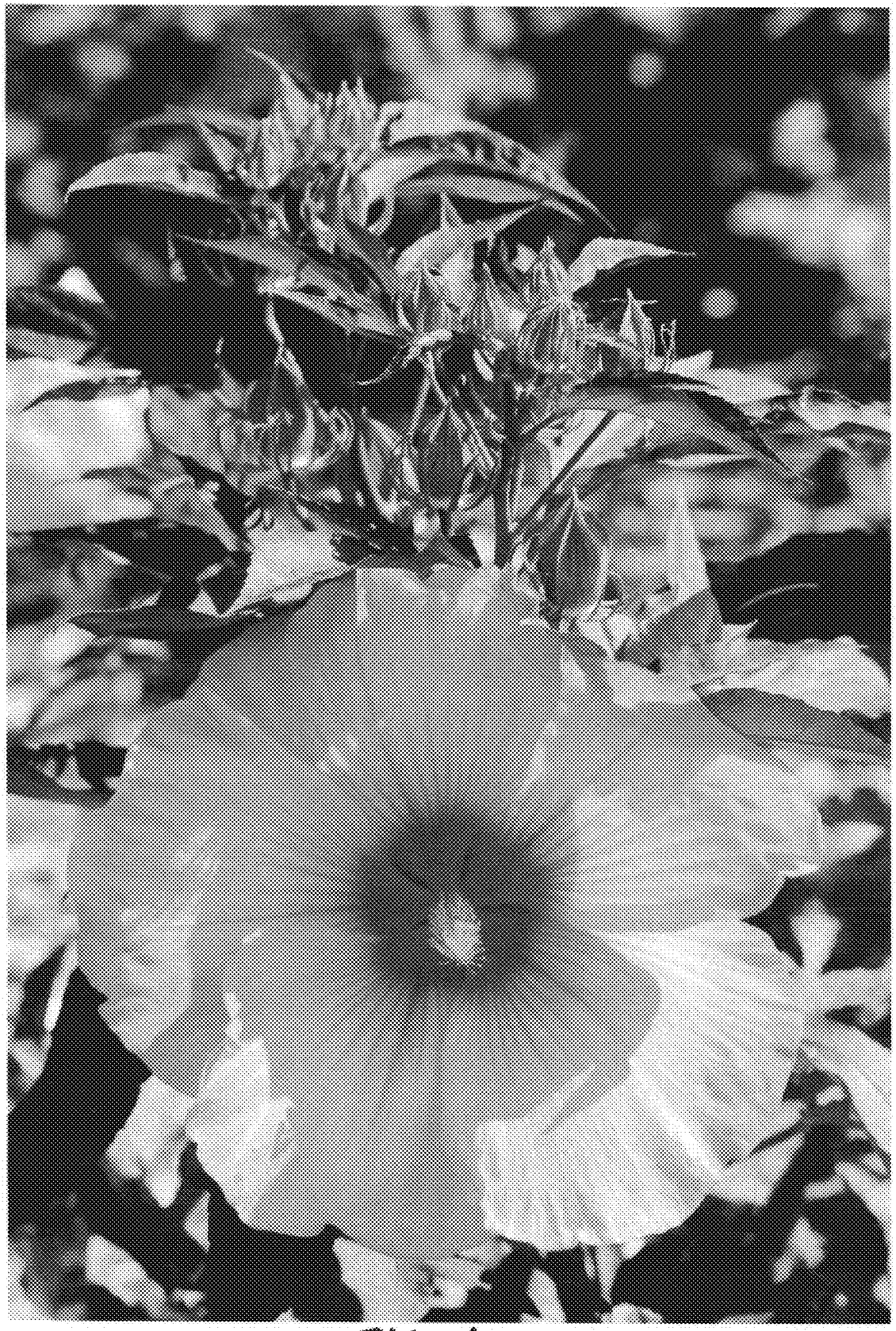
FIG. 1 is a close-up of the flower and the leaf.
Figure 2:
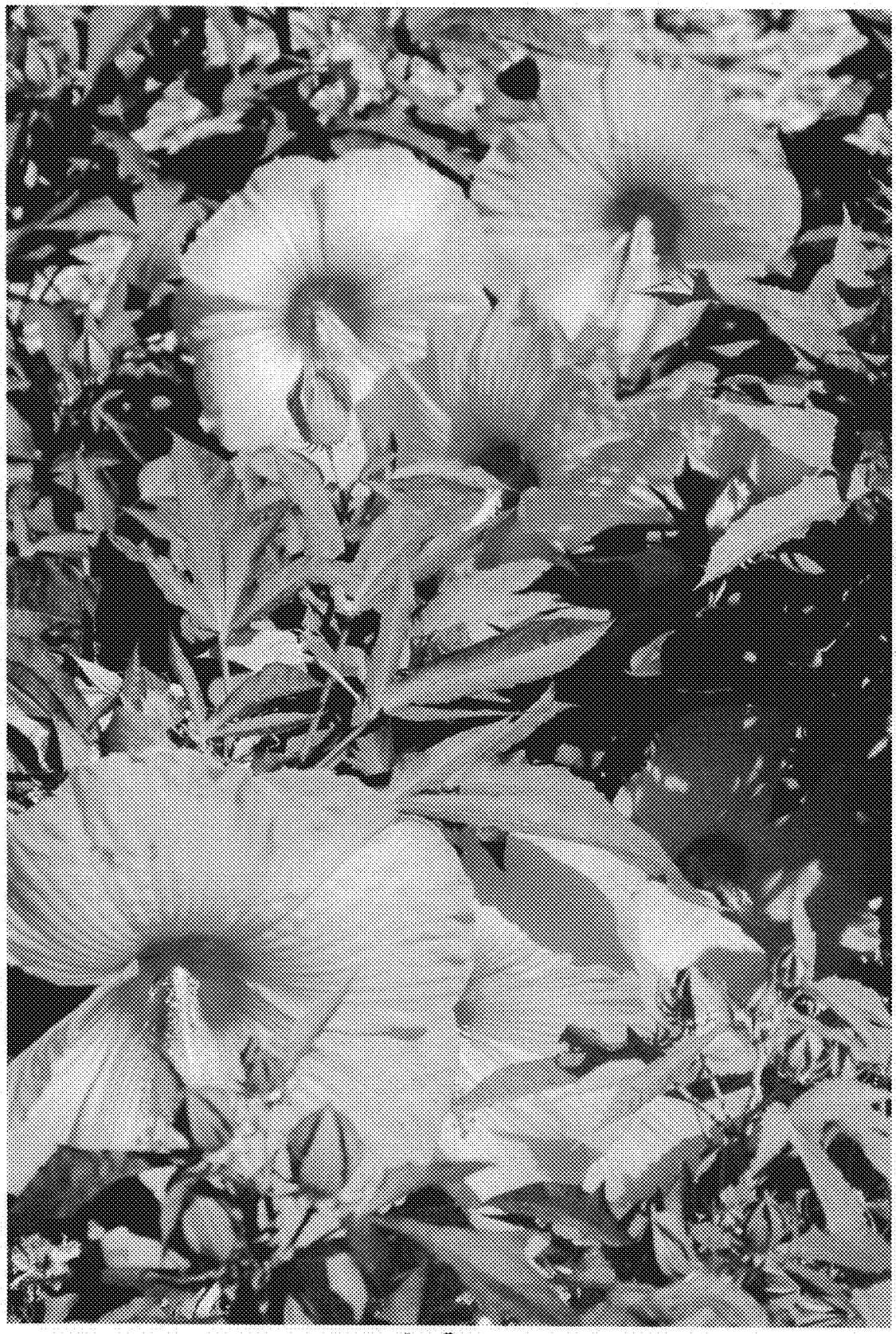
FIG. 2 is a depiction of the whole plant.

The colors are as true as is reasonably possible to attain in photographic illustrations of this type. The colors illustrated may be slightly off due to light reflectance.

DESCRIPTION OF THE NEW PLANT

What follows is a detailed description of the new cultivar. The specific color descriptions are in accordance with The Royal Horticultural Society Colour Chart, while general color recitations are consistent with ordinary American terminology.

'Stardust' has not been observed under all possible environmental conditions. It is to be understood that the phenotype may vary significantly with variations in the environment such as temperature, light intensity, humidity, and day length without, however any difference in genotype of the plant. The following botanical characteristics and observations are gathered from the plant when grown in Lincoln, Nebr. (USDA Zone 4).

THE PLANT

Parentage:

*Seed parent.—Hibiscus moscheutos,* unnamed and unpatented Fleming-bred seedling.

*Pollen parent.*—*Hibiscus coccineus,* unnamed and unpatented Fleming-bred seedling.

Comparison between observed plant and parents: Parents were similar, except for being approximately ½ foot taller in height than Observed Plant.

Comparison between observed plant and other known cultivars: The Observed Plant is unique, but most similar to Co-pending patent application Ser. Nos. 12/317,167, 12/317,182, 12/317,183 and the other patented hardy *Hibiscus* from Flemings Flower Fields, in that:

(a) they are all more compact at 3 feet on average.

(b) they are all hardy to −30 degrees Fahrenheit.

(c) they all have refined new leaf shapes.

(d) they all have thick, overlapping new flower colors with blooms from the top to the bottom of the plant.

Origin: A selected seedling from stated cross.

Type of plant: Hardy, herbaceous perennial.

Classification: Variety of hardy *Hibiscus* plant.

Propagation: Relatively easy to propagate through cuttings; holds its distinguishing characteristics through successive cuttings and divisions.

Size: About 2½ to 3 feet tall and about 2½ feet wide.

Form: Symmetrical annual growth from perennial roots.

Habit: Upright and uniformly branched.

Growth: Vigorous; medium and compact. Full grown (2½ to 3 ft) in 2 years.

Hardiness: Hardy to at least −30 degrees Fahrenheit.

General health: Plant is very disease resistant against rot, aphids, spider mites, scale, white fly etc.; sturdy through excessive drought, rain or wind.

Propagation: Relatively easy and fast rooting in approximately 2 weeks.

Foliage:

1. *Arrangement:.*—Alternate.
2. *Shape.*—Juvenile: 3-5 lobed "maple-shaped" leaves. Rounded base shape. Mature: Refined, "maple-shaped", 3-5 lobed leaf with entire to mildly serrate margins and acute apices; rounded base.
3. *Size.*—Mature leaf (petiole base to apex): Length is about 6½ inches or (17 cm), width is about 5 inches or (13.5 cm). Young leaf: Length 2¾ inches or (7 cm), width is 3 inches or (7.5 cm).
4. *Color.*—Young leaves (upper side): 147 and 148-A; (purple cast): Blend of 175A and N77-A Mature leaves: (upper side): 147 and 148-A. Blend of 175A and N77-A. Veins: 59-A. Venation pattern: Palmate. Venation Color: 59-A and 148-A Coloration of the lower leaf surface: Between 137 and 139C.
5. *Surface texture.*—Upper: Smooth. Lower: Semi-smooth.
6. *Petiole length.*—About 2¾ inches or 6.5 cm. Diameter: 1-2 cm.
7. *Petiole color.*—137-A.

Stems: The stems are stout at the base becoming more slender toward the apices; coloration is consistent with the petiole.

Length: 2-3 inches. Diameter: 1-2 cm.

Internode length: Approximately 2 inches.

Texture: Semi-smooth.

THE FLOWER

Blooming period: Profuse from July until frost.

Flower diameter: Large; about 9-10 inches (24 cm).

Borne: Singly in leaf axils, from midpoint of stems upward.

Bloom duration: Individual bloom lasts at least one to two full days.

Form: Campanulate; petals are also very overlapping.

Average number of flowers per season: 300.

Bud:

1. *Length.*—About 2¼ inches or (6 cm) on day before opening. Diameter: Approximately 2 inches.
2. *Color.*—Between 58-A and 61-B.
3. *Surface texture.*—Semi-glabrous.
4. *Duration.*—One to two weeks.

Corolla: Having five petals.

1. *Petal character and dimensions.*—Campanulate and very overlapping. (a) Length: About 4¾ inches or (12 cm). (b) Width: About 5½ inches or (14 cm).
2. *Coloration.*—Red and pink. 73-A, B and C; 46A, 46B, N 57-A, N-57-C. (a) Markings (Dashes) on petal surface: (Front and back): N57-A and C. Background coloration of petal surface: Between 73A and 73C. (b) Venation (through veins) in petals: 73-B and N-7C. (c) Eye zone: Both 46A and 46B. Size: 2½ inches or (6½ cm).
3. *Texture.*—Smooth.
4. *Substance.*—Thick.
5. *Shape.*—Campanulate and very overlapping with petal folds at edges.

Reproductive organs:

1. *Staminal column.*—Stamen along basal two-thirds. Stamen length: About 1¾ inches or (4.8 cm). Stamen color: Lighter than 11-D with N 74A (streaks). Pollen color: 11-C and B.
2. *Style.*—Terminates upper one-third of stamina column. Stigmatic lobe color: 11-D (tips: 63-A).

Calyx: Connate at the base; about 1¼ inches or (3.5 cm) in length.

*Color.*—Medium green: 147-A.

Stipules: None.

Seed: Size: 1 cm. Color: Grey-brown. Average number: Less than 100.

Epicalyx: Whorl of bracts.

1. *Shape.*—10-12 slender, sword-shaped bractlets.
2. *Length.*—About 1½ inches or (3.8 cm).
3. *Color.*—144-A.

Penduncle:

1. *Length.*—About 2 inches or (6½ cm). Diameter: 1 cm.
2. *Strength.*—Stiff and sturdy.
3. *Color.*—Light to medium green with slight reddish-purple cast. 148-A and 175A.

GENERAL OBSERVATIONS

This plant, as a hybridized hardy *Hibiscus,* is valuable to the landscape market for its improvements in thicker textured and brightly colored flowers and buds, refined "maple-like" foliage with a bronze color, its all-around vigor, good compact breaking action, and adaptation to extreme environments, including the ability to consistently survive winter temperatures of at least −30 degrees Fahrenheit.

The invention claimed is:

1. A new and distinct cultivar of hardy *Hibiscus* plant, as herein shown and described, characterized by its compact nature, refined "maple-shaped" foliage of a bronze coloration, its large heavily streaked and speckled, red and pink flowers, its vigor and its hardiness.

* * * * *